United States Patent
Laga et al.

(10) Patent No.: US 12,263,238 B2
(45) Date of Patent: Apr. 1, 2025

(54) STYLING COMPOSITION FOR PROVIDING VARIOUS ADVANTAGEOUS PROPERTIES TO THE HAIR

(71) Applicant: L'OREAL, Paris (FR)

(72) Inventors: Stephanie Laga, Rahway, NJ (US); Allison Perner, Metuchen, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/957,744

(22) Filed: Sep. 30, 2022

(65) Prior Publication Data

US 2024/0122835 A1    Apr. 18, 2024

(51) Int. Cl.
*A61K 8/60* (2006.01)
*A61K 8/44* (2006.01)
*A61Q 5/06* (2006.01)

(52) U.S. Cl.
CPC .............. *A61K 8/60* (2013.01); *A61K 8/442* (2013.01); *A61Q 5/06* (2013.01)

(58) Field of Classification Search
CPC .......... A61K 8/60; A61K 8/422; A61K 8/891; A61K 8/062; A61K 8/342; A61K 8/345; A61K 8/37; A61K 8/608; A61K 8/737; A61K 8/8147; A61K 8/8182; A61K 8/86; A61K 8/892; A61K 8/922; A61K 2800/5422; A61K 8/8152; A61Q 5/06
See application file for complete search history.

(56) References Cited

U.S. PATENT DOCUMENTS

| | | | |
|---|---|---|---|
| 9,918,922 B1 * | 3/2018 | Botto | A61K 8/60 |
| 2003/0147827 A1 | 8/2003 | Decoster et al. | |
| 2003/0157049 A1 | 8/2003 | Gawtrey et al. | |
| 2007/0154434 A1 | 7/2007 | Decoster et al. | |
| 2007/0154441 A1 | 7/2007 | Gawtrey et al. | |
| 2009/0074697 A1 | 3/2009 | Huynh | |
| 2015/0147285 A1 * | 5/2015 | Mimura | A61K 8/927 424/70.16 |
| 2015/0174023 A1 * | 6/2015 | Washington | A45D 7/04 132/204 |
| 2018/0078474 A1 * | 3/2018 | Biato | A61K 8/891 |
| 2021/0154120 A1 * | 5/2021 | Kadir | A61Q 5/06 |
| 2022/0273551 A1 | 9/2022 | Ye-Tse et al. | |
| 2022/0273552 A1 | 9/2022 | Ye-Tse et al. | |

FOREIGN PATENT DOCUMENTS

| | | | | |
|---|---|---|---|---|
| EP | 3527264 A1 * | 8/2019 | | A61K 8/375 |
| WO | 2021155002 A1 | 8/2021 | | |
| WO | 2022006060 A1 | 1/2022 | | |

OTHER PUBLICATIONS

Ors, Curls Unleashed Coconut and Avocado Does It All Smoothie Styler, Jan. 2022. Retrieved from: https://web.archive.org/web/20220117215946/https://orshaircare.com/products/coconut-and-avocado-curl-smoothie (Year: 2022).*

Lanigan et al, Final report on the safety assessment of EDTA, calcium disodium EDTA, diammonium EDTA, dipotassium EDTA, disodium EDTA, TEA-EDTA, tetrasodium EDTA, tripotassium EDTA, trisodium EDTA, HEDTA, and trisodium HEDTA, 2002, Int J Toxicol, vol. 21, issue 2, pp. 95-142. (Year: 2002).*

Database GNPD [Online]; Mintel Anonymous: "Bodifying Creme Mousse," 2007 XP093064980.

* cited by examiner

*Primary Examiner* — Benjamin J Packard
*Assistant Examiner* — Joshua A Atkinson
(74) *Attorney, Agent, or Firm* — POLSINELLI PC

(57) ABSTRACT

Compositions and methods for styling the hair are provided. The compositions improve the curl definition, softness, smoothness, sensory feel, and/or frizz control to the hair. Also provided are methods of using the compositions.

18 Claims, No Drawings

STYLING COMPOSITION FOR PROVIDING VARIOUS ADVANTAGEOUS PROPERTIES TO THE HAIR

TECHNICAL FIELD

The present disclosure relates to compositions and methods for styling and caring for the hair. The compositions disclosed improve the look and feel of the hair. The disclosure also relates to methods of using the compositions.

BACKGROUND

Consumers desire new and improved styling compositions that can deliver visible curl definition and frizz control in high humidity environments, while also providing various additional advantageous properties to the hair such as good curl definition, curl hold, hair moisture, softness, and smoothness.

It is an objective of the present invention to provide a composition containing a chelating agent and sugar that provides enhanced curl definition, frizz control, and a good sensory feel to the hair even under high humidity environments.

SUMMARY

The present disclosure relates to compositions for styling the hair, which may provide beneficial effects, such a curl definition, to the hair. The compositions are optionally leave-in hair styling compositions. The compositions may comprise (a) at least one chelating agent; (b) at least one sugar; and (c) at least one cosmetically acceptable solvent, wherein the pH of the composition is between 3 and 9.

The present disclosure relates to a method for styling and or caring for hair comprising applying to the hair a composition comprising: (a) at least one chelating agent (b) at least one sugar (c) at least one cosmetically acceptable solvent.

The present disclosure relates to a hair styling composition, comprising: (a) at least one chelating agent (b) at least one cosmetically acceptable solvent, wherein the chelating agent is about 1% to about 7% of the total composition.

Chelating agents are typically used in hair products to bind metal ions present in the water or product for improved stability and/or performance. The applicant was surprised to discover good curl definition resulting from a chelating agent.

Particularly, it was surprisingly and unexpectedly discovered that the combination of chelating agent and sugar together provide the complete results of enhanced curl definition, frizz control, and a good sensory feel to the hair, whereas these components alone only provide some benefits but not all.

In other words, the inventors of the present application have developed a new and improved styling composition for curly hair which withstands high humidity conditions.

DETAILED DESCRIPTION

The disclosure relates to compositions for styling hair, such as for curl definition, frizz control, and/or improved sensory feel of the hair, as well as methods of using the compositions.

I. Compositions

In various embodiments, compositions according to the disclosure comprise (a) at least one chelating agent; (b) at least one sugar; (c) at least one cosmetically acceptable solvent; wherein the pH ranges from 3 to 9.

Chelating Agents

Compositions according to the disclosure comprise at least one chelating agent.

According to preferred embodiments of the present invention, compositions further comprising at least one chelating agent are provided. Such chelating agents are known in the art and described, for example, in "Chelating agents" Kirk Othmer Encyclopedia of Chemical Technology, Vol. 5 pp. 708-739, published in 2003 and subsequent editions.

Suitable chelating agents include, but are not limited to, polyphosphates, aminocarboxylic acids, 1,3-diketones, hydroxycarboxylic acids, polyamines, amino alcohols, heterocyclic aromatic bases, aminophenols, Schiff's bases, tetrapyrroles, sulfur compounds, synthetic macrocyclic compounds, polymers and phosphonic acids. Preferably, chelating agents are selected from aminocarboxylic acids.

Specific examples of suitable chelating agents include, but are not limited to, ethylenediaminetetraacetic acid (EDTA), tetrasodium etidronate, tetrasodium pyrophosphate, pentasodium ethylenediamine tetramethylene phosphonate, sodium staminate, tetrasodium glutamate diacetate, tetraacetic acid, DPTA (1,3-diaminopropanetetraacetic acid), and mixtures thereof.

Preferred embodiments in this disclosure include trisodium ethylenediamine disuccinate, tetrasodium glutamate diacetate, disodium cocoamphodiacetate, trisodium HEDTA.

In various exemplary embodiments, the at least one chelating agent may be present in the compositions in an amount of about 0.1% or more by weight, such as about 0.2% or more, about 1% or more or about 2% or more by weight, relative to the total weight of the composition. In other embodiments, at least one chelating agent may be present in the compositions in an amount up to about 10%, such as up to about 9%, up to about 8%, up to about 7%, up to about 6%, up to about 5%, up to about 4%, up to about 3%, up to about 2%, up to about 1%, relative to the total weight of the composition. By way of non-limiting example, the at least one chelating agent is present in the composition with a total amount ranging from about 0.1% to about 10%, by weight, for example, from about 0.1% to about 9%, from about 0.1% to about 8%, from about 0.1% to about 7%, from about 0.1% to about 6%, from about 0.1% to about 5%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, by weight, relative to the total weight of the composition. In one embodiment, the at least one chelating agent is present in an amount ranging from about 0.1% to about 10%, preferably from about 0.2% to about 5% by weight, relative to the total weight of the composition, including all ranges and subranges thereof.

Sugar

Compositions according to the disclosure comprise at least one sugar. The term "sugar" as used herein is intended to mean oxygen-bearing hydrocarbon-based compounds containing several alcohol functions, with or without aldehyde or ketone functions, and which comprise at least 4 carbon atoms. These sugars may be monosaccharides, disaccharides, oligosaccharides or polysaccharides, and derivatives thereof, such as amine derivatives, for instance glucosamine. The term "sugar" may also encompass sugar alcohols.

An embodiment of the sugar derivative is hydrogenated starch hydrolysate. The term "hydrogenated starch hydrolysate" as used herein is intended to mean a sugar or sugar alcohol that is formed by the controlled hydrogenation of a hydrolyzed starch. The hydrogenated starch hydrolysate can include but is not limited to several sugar alcohols including sorbitol, mannitol, isomalt, maltitol, lactitol, xylitol, erythritol or mixtures thereof.

Preferred representative examples of the hydrogenated starch hydrolysate include MERITOL® 160 supplied by Syral, NEOSORB® 70/70B supplied by Roquette or BEAUTÉ BY ROQUETTE® PO 070 supplied by Roquette.

In an embodiment, the sugar is chosen from C4-C6 monosaccharides.

In an embodiment, the sugar is chosen from pentoses and derivatives thereof. In a further embodiment, the pentoses are chosen from xylose, arabinose, ribose, 2-deoxy-ribose, ribulose, deoxy-ribulose, arabinose, xylulose, or mixtures thereof.

In an embodiment, the sugar is chosen from hexoses and derivatives thereof, such as amino hexoses. In a further embodiment, the hexoses are chosen from allose, altrose, glucose (including dextrose), glucosamine, mannose, gulose, idose, galactose, talose, sorbose, psicose, fructose, tagatose, or mixtures thereof.

In an embodiment, the sugar is chosen from disaccharides (which are saccharides that hydrolyze into two monosaccharides). In a further embodiment, the disaccharides are chosen from sucrose (also saccharose), maltose, lactose, cellobiose, trehalose, dextran, or mixtures thereof.

In an embodiment, the sugar is chosen from polysaccharides (which are saccharides that hydrolyze into more than two monosaccharides). In a further embodiment, the polysaccharides are chosen from maltotriose, starch, dextrins, cellulose, glycogen, or mixtures thereof.

In an embodiment, the sugar may be chosen from any aldoses or ketoses or tetroses or teioses or aldotetroses (such as erythrose and treose), ketotetroses (such as erythrulose), aldotrioses (such as glyceraldehyde) and ketotrioses (such as dihydroxyacetone), or furanoses, N-acetyl-D-galactosamine, N-acetyl-D-glucosamine, N-acetylneuraminic acid, adonitol, beta-D-allose, D-altrose, 6-amino-6-deoxy-D-glucose, 1,6-anhydro-glucose, arabinic acid, arabinogalactan, D-arabinose, L-arabinose, D,L-arabinose, D-arabitol, L-arabitol, D-cellobiose, D-glucosamine, D-galactosamine, 2-deoxy-D-glucose, 6-deoxy-D-galactose, 6-deoxy-L-galactose, galactitol, mesoerythritol, D-erythroe, D-fructose, D-fucose, L-fucose, D-galactaric acid, galactitol, galactomannan, D-galactono-1,4-lactone, L-galactono-1,4-lactone, D-galactosarmine, D-galactose, L-galactose, D-galacturonic acid, beta-gentiobiose, glucamine, D-glucaric acid, D-glucono-1,5-lactone, L-glucono-1,5-lactone, D-glucosaminic acid, D-glucuronic acid, L-glucose, D-glucose, isomaltitol, isomaltotriose, isomaltose, lactobionic acid, D-lactose, lactulose, D-lyxose, L-lyxose, lyxosamine, maltitol, D-maltose, maltotetraose, maltotriitol, maltotriose, D-mannosamine, D-mannose, L-mannose, D-melezitose, D-melibiose, D-raffinose, D-raffinose undecaacetate, L-rhamnose, D-ribose, L-ribose, D-ribulose, rutinose, D-sucrose, alpha-sophorose, sorbitol, D-tagatose, D-talose, D-threose, turanose, D-xylitol, D-xylose, L-xylose and D,L-xylose.

Preferred embodiments of this disclosure are sugars chosen from glucose, erythritol, glucosamine HCl, hydrogenated starch hydrolysate, or combinations thereof.

In various exemplary embodiments, the at least one sugar may be present in the compositions in an amount of about 0.1% or more by weight, such as about 0.2% or more, or about 0.5% or more by weight, relative to the total weight of the composition. In other embodiments, at least one sugar may be present in the compositions in an amount up to about 5%, such as up to about 4%, up to about 3%, up to about 2%, relative to the total weight of the composition. In one embodiment, the at least one sugar is present in an amount ranging from about 0.1% to about 5%, preferably from about 0.2% to about 2% by weight, relative to the total weight of the composition, including all ranges and subranges thereof.

In a preferred embodiment, the at least one sugar is present in an amount ranging from about 0.5% to about 2%.

Cosmetically Acceptable Solvents

Compositions according to the disclosure comprise at least one cosmetically acceptable solvent. The solvent may comprise water, non-aqueous solvents, or mixtures thereof.

In some embodiments, the solvent comprises, consists essentially of, or consists of water. The total amount of water in the compositions may vary depending on the type of composition and the desired consistency, viscosity, etc.

In certain embodiments, the composition comprises one or more non-aqueous solvents, other than or in addition to ingredients discussed above. For example, C1-4 alcohols, organic solvents, fatty alcohols, fatty ethers, fatty esters, polyols other than those described above, glycols, vegetable oils, mineral oils, liposomes, laminar lipid materials, or any a mixture thereof. Non-limiting examples of solvents which may be used include alkane polyols such as 1,2,6-hexanetriol, trimethylolpropane, butylene glycol, ethylene glycol, propylene glycol, diethylene glycol, hexylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; alkyl alcohols having 1 to 4 carbon atoms such as ethanol, methanol, butanol, propanol, and isopropanol (isopropyl alcohol); glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbitol, sorbitan, acetine, diacetine, triacetine, sulfolane, or mixtures thereof.

Preferred embodiments of the disclosure are solvents selected from butylene glycol, water, glycerin, ethylhexylglycerin, or combinations thereof.

The solvent may be present in the composition in an amount ranging from about 70% to about 99% by weight, relative to the total weight of the composition, including all ranges and subranges therebetween. For example, in one embodiment, the total amount of solvent may be about 70% to about 95%, about 80% to about 95%, or about 85% to about 90% by weight, relative to the total weight of the composition. In certain embodiments, the solvent is primarily comprised of water, such as from about 90% to about 99%, or about 95% to about 99%, of the total solvent.

Additional Components Compositions according to the disclosure may optionally include any additional component suitable for use in such compositions. Such components may include, but are not limited to, fatty compounds, polymers, and surfactants.

Surfactants

Compositions according to the disclosure may optionally include at least one surfactant. The at least one surfactant may be selected from anionic surfactants, nonionic surfactants, amphoteric surfactants, or mixtures thereof.

The total amount of the at least one surfactant included in the composition typically ranges from about 0.01% to about 15% by weight, relative to the total weight of the composition, including all ranges and subranges therebetween.

Anionic Surfactants

The term "anionic surfactant" means a surfactant comprising, as ionic or ionizable groups, only anionic groups. These anionic groups may optionally be chosen from the groups $CO_2H$, $CO_2^-$, $SO_3H$, $SO_3^-$, $OSO_3H$, $OSO_3^-O_2PO_2H$, $O_2PO_2H$ and $O_2PO_2^{2-}$.

The compositions may include one or more anionic surfactants. Non-limiting examples of anionic surfactants include alkyl sulfates, alkyl ether sulfates, acyl isethionates, acyl glycinates, acyl taurates, acyl amino acids, acyl sarcosinates, sulfosuccinates, sulfonates, and a mixture thereof, wherein the alkyl and acyl groups of all these compounds comprise from 6 to 24 carbon atoms.

The total amount of the one or more anionic surfactants may be about 0.01% to about 15% by weight, relative to the total weight of the composition, including all ranges and subranges therebetween.

Non-Ionic Surfactants

Non-ionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The non-ionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_4$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and a mixture thereof Examples of oxyalkylenated nonionic surfactants that may be mentioned include: oxyalkylenated ($C_8$-$C_4$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, condensates of ethylene oxide and/or of propylene oxide, inter alia, alone or as mixtures.

The nonionic surfactants may preferably be chosen from glyceryl stearate, PEG-100 stearate, or combinations thereof.

The total amount of the one or more nonionic surfactants may be about 0.01% to about 15% by weight, relative to the total weight of the composition, including all ranges and subranges therebetween. For example, in one embodiment the nonionic surfactant is present in an amount ranging from about 1% to about 3%.

Amphoteric Surfactants

Non-limiting examples of amphoteric surfactants useful in the compositions include, for example, optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

The total amount of the one or more amphoteric surfactants may be about 0.01% to about 15% by weight, relative to the total weight of the composition, including all ranges and subranges therebetween.

Fatty Compounds

Compositions according to the disclosure may optionally include at least one fatty compound.

Fatty compounds (also referred to interchangeably as "fatty substances") may be included in one or more embodiments of the invention. In some embodiments, two or more fatty compounds may be included. In further embodiments, such fatty compounds may be a fatty compounds other than a fatty acid. As used herein, "fatty compound" means an organic compound insoluble in water at normal temperature (25° C.) and at atmospheric pressure (760 mmHg) (solubility below 5% and such as below 1% and further such as below 0.1%). Fatty compounds have in their structure a chain of at least two siloxane groups or at least one hydrocarbon chain having at least 6 carbon atoms. Moreover, fatty compounds are generally soluble in organic solvents in the same conditions of temperature and pressure, for example in chloroform, ethanol, benzene or decamethylcyclopentasiloxane.

Fatty compounds are, for example, chosen from lower alkanes, fatty alcohols, esters of fatty acid, esters of fatty alcohol, oils such as mineral, vegetable, animal and synthetic non-silicone oils, non-silicone waxes and silicones.

In some embodiments, the alcohols and esters have at least one linear or branched, saturated or unsaturated hydrocarbon group, comprising 6 to 30 carbon atoms, optionally substituted, for example, with at least one hydroxyl group (for example 1 to 4). If they are unsaturated, these compounds can have one to three, conjugated or unconjugated, carbon-carbon double bonds.

With regard to the lower alkanes, in some embodiments, these have from 6 to 16 carbon atoms and are linear or branched, optionally cyclic. As examples, alkanes can be chosen from hexane and dodecane, isoparaffins such as isohexadecane and isodecane.

The fatty compounds may preferably be chosen from isopropyl myristate, *Ricinus communis* seed oil, cetearyl alcohol, cetyl esters or combinations thereof.

The total amount of the at least one fatty compounds may be about 0.01 to about 30% by weight, relative to the total weight of the composition, including all ranges and subranges therebetween. For example, in one embodiment the at least one fatty compound is present in an amount ranging from about 12% to about 17%.

Polymers

Compositions according to the disclosure may optionally include at least one polymer. By way of non-limiting example, the polymers that can be used in the disclosure may be chosen from cationic polymers. In some instances, the polymers may be selected from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquaterniums, and a mixture thereof. Mention may be made more particularly of the following cationic polymers:

(1) homopolymers or copolymers derived from acrylic or methacrylic esters or amides and comprising at least one of the following units (A)-(D):

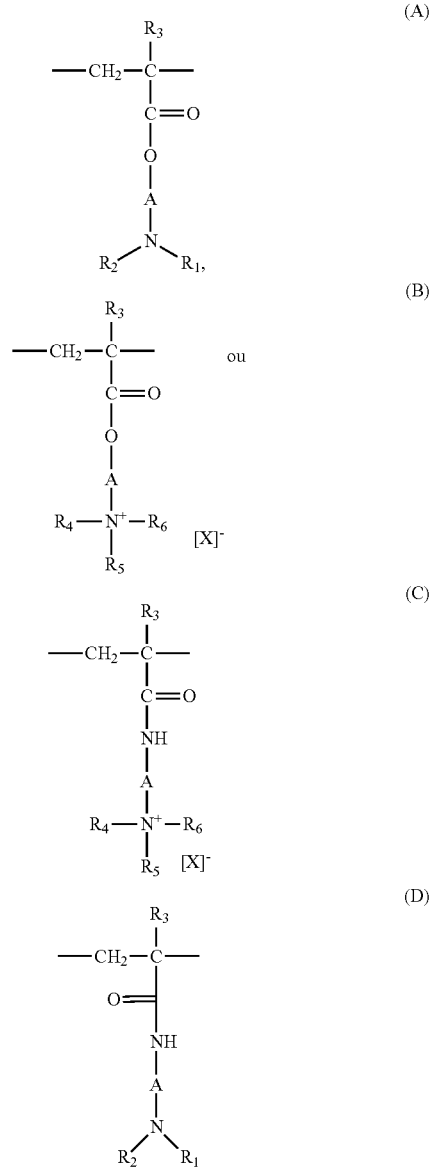

in which:

$R_3$ denotes a hydrogen atom or a $CH_3$ radical;

A is a linear or branched alkyl group comprising from 1 to 6 carbon atoms or a hydroxyalkyl group comprising from 1 to 4 carbon atoms;

$R_4$, $R_5$ and $R_6$, which may be identical or different, represent an alkyl group having from 1 to 18 carbon atoms or a benzyl radical;

$R_1$ and $R_2$, which may be identical or different, each represent a hydrogen atom or an alkyl group having from 1 to 6 carbon atoms; and X denotes a methosulfate anion or a halide such as chloride or bromide.

The copolymers of family (1) also contain one or more units derived from comonomers that may be chosen from the family of acrylamides, methacrylamides, diacetone acrylamides, acrylamides and methacrylamides substituted on the nitrogen with lower ($C_1$-$C_4$) alkyl groups, groups derived from acrylic or methacrylic acids or esters thereof, vinyl-lactams such as vinylpyrrolidone or vinylcaprolactam, and vinyl esters. Thus, among these copolymers of family (1), mention may be made of:

quaternized or non-quaternized vinylpyrrolidone/dialkylaminoalkyl acrylate or methacrylate copolymers, such as the products sold under the name Gafquat® by the company ISP, for instance Gafquat® 734 or Gafquat® 755 or Gafquat® 755N (INCI name Polyquaternium-11), or alternatively the products known as Copolymer® 845, 958 and 937 sold by ISP (INCI name VP/dimethylaminoethyl methacrylate copolymer). These polymers are described in detail in French patents 2077143 and 2393573;

fatty-chain polymers containing a vinylpyrrolidone unit, such as the products sold under the name Styleze® W20L and Styleze® W10 by the company ISP (INCI name Polyquaternium-55);

dimethylaminoethyl methacrylate/vinylcaprolactam/vinylpyrrolidone terpolymers, such as the products sold under the names Advantage HC 37 or Gaffix® VC 713 by the company ISP (INCI name Vinyl caprolactam/VP/dimethylaminoethyl methacrylate copolymer); and quaternized vinylpyrrolidone/dimethylaminopropylmethacrylamide copolymers, such as the products sold under the name Gafquat® HS 100 by the company ISP (name Polyquaternium-28);

(2) cationic guar gum derivatives, preferably containing quaternary ammonium, such as those described in U.S. Pat. Nos. 3,589,578 and 4,031,307, such as guar gums containing trialkylammonium cationic groups. Such products are sold in particular under the trade names Jaguar® C13 S, Jaguar® C 15 and Jaguar® C 17 by the company Rhodia (INCI name Guar hydroxypropyltrimonium chloride);

(3) quaternary copolymers of vinylpyrrolidone and of vinylimidazole; mention may be made, for example, of vinylpyrrolidone/methylvinylimidazolium chloride copolymers, such as the products sold by the company BASF under the names Luviquat® FC550 or FC370, Luviquat® Excellence and Luviquat® Style (INCI name Polyquaternium-16), or vinylpyrrolidone/vinylimidazolium methosulfate/vinylcaprolactam terpolymers, such as the product Luviquat® Hold sold by the company BASF (INCI name Polyquaternium-46);

(4) chitosans or salts thereof; the salts that can be used are, in particular, chitosan acetate, lactate, glutamate, gluconate or pyrrolidonecarboxylate. Among these compounds, mention may be made of the chitosan pyrrolidonecarboxylate sold under the name Kytamer® PC by the company Amerchol (INCI name Chitosan PCA); and (5) cationic cellulose derivatives such as copolymers of cellulose or of cellulose derivatives grafted with a water-soluble monomer comprising a quaternary ammonium, and described in particular in U.S. Pat. No. 4,131,576, such as hydroxyalkylcelluloses, for instance hydroxymethyl-, hydroxyethyl- or hydroxypropylcelluloses grafted in particular with a methacryloyloxy-ethyltrimethylammonium, methacrylamidopropyltrimethyl-ammonium or dimethyldiallylammonium salt. The commercial products corresponding to this definition are, more particularly, the products sold under the name Celquat® L 200 and Celquat® H 100 by the company Akzo Nobel (INCI name Polyquaternium-4).

In some instances, the polymers may be selected from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquaterniums, and a mixture thereof.

In certain embodiments, the polyquaterniums may be selected from polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-37, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc.

The polymers may preferably be chosen from VP/dimethylaminoethyl methacrylate copolymer, polyquaternium-37, or combinations thereof.

The total amount of the at least one polymer may be about 0.01% to about 15% by weight, relative to the total weight of the composition, including all ranges and subranges therebetween. For example, in one embodiment the polymer is present in an amount ranging from about 2% to about 6%.

Terms

As used herein, the term "styled" is intended to include "shaped."

As used herein, the term "curly hair" refers to any hair including a curl. The curl may be natural or unnatural, i.e., formed by chemical treatment or physical treatment of the hair. The degree of curliness of the hair may vary and is not limited.

As used herein, "frizz" refers to hair with fibers that are not uniformly aligned and/or contain stray hair fibers.

As used herein, hair with improved or enhanced curl definition may have curls with a shape that has a clean ringlet appearance rather than being frizzy, curls that appear more individualized, curls that are more closed in appearance, and/or curls that have an improved visual appearance of the hair color and/or highlights.

A "leave-in" composition or product refers to a composition such as a hair-treatment composition that is not rinsed and/or washed away with water or acceptable solvent after the application of the composition onto the keratin fiber, such as hair; instead, the composition is allowed to remain on the keratin fibers for a period of time as desired, such from 1 hour, 2 hours, 3 hours, 4 hours, up to 8 hours, overnight, or as long as needed, until next time of washing or rinsing the keratin fibers.

EXAMPLES

The following examples are intended to be non-limiting and explanatory in nature only. In the Examples, amounts are expressed in percentage by weight (wt %) of active materials, relative to the total weight of the composition.

Example 1—Simplex Testing for Chelating Agent

In order to demonstrate the beneficial effects of chelating agents according to the disclosure on curly hair, the following compositions of water with varying chelating agents (B-E) and a comparative composition of no chelating agent (A) were prepared.

TABLE 1

Chelating Agent Compositions

| Sample | Chelating Agent | % Chelating Agent | Water |
|---|---|---|---|
| A | Water only | 0% | 100% |
| B | Trisodium HEDTA | 5% | 95% |
| C | Trisodium ethylenediamine disuccinate | 5% | 95% |
| D | Disodium cocoamphodiacetate | 5% | 95% |
| E | Tetrasodium glutamate diacetate | 5% | 95% |

Each of compositions A-E were tested on five natural, curly hair swatches. Each hair swatch was first washed with a commercially available shampoo and detangled. The swatches were then air dried, and sprayed with water five times per swatch. While the swatches were still damp, equal amounts of a testing composition was applied to each hair swatch and then styled. After the swatches air dried, they were put into a humidity chamber at 80% relative humidity at 25° C. for one hour.

After one hour in the humidity chamber, the treated swatches were qualitatively assessed for curl definition, frizz control, and sensory profile. A rating of 1-5 was provided for frizz control and curl definition, where 1 represented the least amount of frizz control/curl definition and 5 represented the most frizz control/curl definition. The sensory profile was determined by manually palpating each swatch. A description of coated was given when the hair had a coated feel which was a neutral description.

The following Table 2 shows the results of assessment and scores of the visual properties of the hair swatches treated with the testing compositions.

TABLE 2

| | | | C | D | E |
| | | B | Trisodium | Disodium | Tetrasodium |
| Chelating | A | Trisodium | ethylenediamine | cocoampho- | glutamate |
| Agent | none | HEDTA | disuccinate | diacetate | diacetate |
|---|---|---|---|---|---|
| Curl Definition* | 2 | 5 | 5 | 5 | 5 |
| Frizz Control* | 2 | 4 | 4 | 5 | 5 |
| Sensory Profile | smooth | coated | coated++ | coated | coated |

*Scale from 1 to 5, where 1 = least amount of curl definition/frizz control and 5 = most amount of curl definition/frizz control As shown in Table 1 and 2, various chelating agents alone deliver excellent curl definition and frizz control compared to the swatches treated without chelating agent. The swatches with chelating agent applied had a coated feel compared to the swatches without chelating agent.

Example 2. Sugar and Chelating Agent Combination Testing

In order to demonstrate the beneficial effects of chelating agent in combination with various sugars according to the disclosure on curly hair, the following compositions of water with varying chelating agent/sugar combinations (G-L) and a comparative compositions of F, N, and V were prepared. Testing was done within the pH range of 3 to 9.

TABLE 3

Sugar and Chelating Agent Combinations

| Sample | Sugar at 1% | Chelating Agent at 0.5% | Water |
|---|---|---|---|
| F | none | none | 100% |
| G | Glucose | Disodium cocoamphodiacetate | 98.5% |
| H | Erythritol (Fisher) | Disodium cocoamphodiacetate | 98.5% |
| I | Glucosamine HCl | Disodium cocoamphodiacetate | 98.5% |
| J | Hydrogenated starch hydrolysate | Disodium cocoamphodiacetate | 98.5% |
| K | Hydrogenated starch hydrolysate | Trisodium ethylenediamine disuccinate | 98.5% |
| L | Hydrogenated starch hydrolysate | Tetrasodium glutamate diacetate | 98.5% |
| N | Hydrogenated starch hydrolysate | none | 99% |
| V | none | Disodium cocoamphodiacetate | 99.5% |

Each composition in the above table was tested on natural, curly hair swatches. Each hair swatch was first washed with a commercially available shampoo and detangled. The swatches were then air dried, and sprayed with water five times per swatch. While the swatches were still damp, equal amounts of a testing composition were applied to each hair swatch and then styled. After the swatches air dried, they were put into a humidity chamber at 80% relative humidity at 25° C. for one hour.

After one hour in the humidity chamber, the treated swatches were qualitatively assessed for curl definition, frizz control, and sensory profile. A rating of 1-5 was provided for frizz control and curl definition, where 1 represented the least amount of frizz control/definition and 5 represented the most. The sensory profile was determined by manually palpating each swatch. A description of coated was given when the hair had a coated feel which was a neutral description.

The following Table 4 shows the results of assessment and scores of the visual properties of the hair swatches treated with the testing compositions.

TABLE 4

Assessment after humidity chamber

| Sample | Definition* | Frizz control* | Sensory profile |
|---|---|---|---|
| F | 1 | 1 | Uncoated, feel fiber |
| G | 3 | 4 | Smooth, buttery coated feel |
| H | 4 | 3 | Smooth, buttery coated feel |
| I | 4 | 2 | Buttery feel, but some drag on hair |
| J | 5 | 5 | Smooth, buttery coated feel |
| K | 4 | 4 | Similar to E but slightly less |
| L | 4 | 4 | Some slip, but not buttery |
| N | 2 | 2 | Very smooth, has slip |
| V | 1 | 1 | Slightly waxy, slight drag |

*Scale from 1 to 5, where 1 = least amount of curl definition/frizz control and 5 = most amount of curl definition/frizz control As shown in Table 4, the synergy of sugar and chelating agent provided curl definition, frizz control and an improved sensory feel as shown in examples G through L. Sample J was the most effective using hydrogenated starch hydrolysate as the sugar and disodium cocoamphodiacetate as the chelating agent to provide optimal frizz control and curl definition while also providing a smooth, buttery coated feel to the hair. The control samples F, N, and V all rated the lowest for curl definition and frizz control.

The results in this example demonstrate that the synergy of the chelating agent and the sugar provides superior frizz control, curl definition, and sensory feel to the hair compared to compositions with chelating agents or sugars alone.

Example 3. Optimal Concentration of Chelating Agent with Sugar

In order to demonstrate the optimal concentration of chelating agents in combination with sugar according to the disclosure on curly hair, the following compositions of water with varying concentration of chelating agents and 1% sugar (O-S) and control compositions (N, T and U) were prepared.

TABLE 5

Sugar and Chelating Agent Compositions

| Sample | Disodium Cocoamphodiacetate % | Hydrogenated Starch Hydrolysate % | Water |
|---|---|---|---|
| N | 0 | 1% | 99% |
| O | 0.2% | 1% | 98.8% |
| P | 0.5% | 1% | 98.5% |
| Q | 2% | 1% | 97% |
| R | 5% | 1% | 94% |
| S | 10% | 1% | 89% |
| T | 0.5% | 0 | 99.5% |
| U | Water only | — | 100% |

Each composition listed in Table 5 was tested on natural, curly hair swatches. Each hair swatch was first washed with a commercially available shampoo and detangled. The swatches were then air dried, and sprayed with water five times per swatch. While the swatches were still damp, equal amounts of a testing composition was applied to each hair swatch and then styled. After the swatches air dried, they were put into a humidity chamber at 80% relative humidity at 25° C. for one hour.

After one hour in the humidity chamber, the treated swatches were qualitatively assessed for curl definition, frizz control, and sensory profile. A rating of 1-5 was provided for frizz control and curl definition, where 1 represented the least amount of frizz control/definition and 5 represented the most. The sensory profile was determined by manually palpating each swatch. A description of coated was given when the hair had a coated feel which was a neutral description.

The following Table 6 shows the results of assessment and scores of the visual properties of the hair swatches treated with the testing compositions.

TABLE 6

Assessment after humidity chamber

| Sample | Definition | Frizz control | Sensory profile |
|---|---|---|---|
| N | 2 | 2 | Very smooth, has slip |
| O | 4 | 4 | Smooth, buttery coated feel |
| P | 4 | 4 | Smooth, buttery coated feel |
| Q | 3 | 3 | Waxy, high drag |
| R | 4 | 4 | Extremely waxy, very high drag |
| S | 4 | 5 | Extremely waxy, very high drag |
| T | 2 | 1 | Slightly waxy, minor drag |
| U | 2 | 1 | Feel hair fiber, but smooth |

*Scale from 1 to 5, where 1 = least amount of curl definition/frizz control and 5 = most amount of curl definition/frizz control As shown in Table 6, an optimal range of chelating agent was found. All of the swatches with the combination of chelating agent and sugar (O-S) showed better curl definition and frizz control in comparison to control swatches N, T, and U. At a 2% loading level and above of disodium cocoamphodiacetate, a waxy coating was observed on the hair and a high amount of drag was seen in swatches Q-S. Swatches O and P provided the ideal sensory feel with a loading level of 0.2% and 0.5% of chelating agent.

The results in this example demonstrate the ideal loading level of chelating agent is between 0.2% and 0.5% when combined with sugar. When combined with an ideal loading level of sugar, the hair has good frizz control, curl definition, and a good sensory feel.

Example 4. Optimal Concentration of Sugar

In order to demonstrate the optimal concentration of sugar according to the disclosure on curly hair, the following compositions of water with varying concentration of sugars and 0.5% chelating agent (W-AA) and a comparative composition of no sugar (V and AB) were prepared.

TABLE 7

Chelating Agent and Sugar Compositions

| Sample | Disodium cocoampho-diacetate % | Hydrogenated starch hydrolysate % | Water |
|---|---|---|---|
| V | 0.5% | 0% | 99.5% |
| W | 0.5% | 0.5% | 99% |
| X | 0.5% | 1% | 98.5% |
| Y | 0.5% | 5% | 94.5% |
| Z | 0.5% | 10% | 89.5% |
| AA | 0% | 1% | 99% |
| AB | Water only | — | 100% |

Each of compositions V-AB were tested on natural, curly hair swatches. Each hair swatch was first washed with a commercially available shampoo and detangled. The swatches were then air dried, and sprayed with water five times per swatch. While the swatches were still damp, equal amounts of a testing composition was applied to each hair swatch and then styled. After the swatches air dried, they were put into a humidity chamber at 80% relative humidity at 2500 for one hour.

After one hour in the humidity chamber, the treated swatches were qualitatively assessed for curl definition, frizz control, and sensory profile. A rating of 1-5 was provided for frizz control and curl definition, where 1 represented the least amount of frizz control/definition and 5 represented the most. The sensory profile was determined by manually palpating each swatch. A description of coated was given when the hair had a coated feel which was a neutral description.

The following Table 8 shows the results of assessment and scores of the visual properties of the hair swatches treated with the testing compositions.

TABLE 8

Assessment after humidity chamber

| Sample | Curl Definition* | Frizz Control* | Sensory Profile |
|---|---|---|---|
| V | 1 | 1 | Slightly waxy, minor drag |
| W | 3 | 3 | Smooth, buttery coated feel |
| X | 3 | 3 | Smooth, buttery coated feel |
| Y | 3 | 2 | Some drag, stiff feeling |
| Z | 3 | 2 | Very high drag, very stiff film |
| AA | 2 | 2 | Smooth root to tip, has slip |
| AB | 1 | 1 | Feel hair fiber, but smooth |

*Scale from 1 to 5, where 1 = least amount of curl definition/frizz control and 5 = most amount of curl definition/frizz control As shown in Table 8, an optimal range of sugar was demonstrated. All of the swatches with the combination of chelating agent and sugar (W-Z) showed better curl definition and frizz control in comparison to control swatches V, AA, and AB. Swatches Y and Z with a higher loading level of sugar showed good frizz control and curl definition, and had a stiff feeing to the hair. Swatches W and X had the best results of good frizz control, curl definition, and a smooth buttery feeling at a loading level of 0.5% and 1% of sugar.

The results in this example demonstrate the ideal loading level of sugar is between 0.5% and 1%. When combined with an ideal loading level of chelating agent, the hair has good frizz control, curl definition, and a good sensory feel.

Example 5. Formulation Testing

In order to demonstrate the invention in a typical hair formulation according to the disclosure on curly hair, the following compositions of comparative and inventive formulations were prepared.

TABLE 9

| Formulations prepared | | |
|---|---|---|
| INCI Name | Comparative Example 1 | Inventive Example 2 |
| Water | QS to 100 | QS to 100 |
| Fatty Compounds | 15.5 | 15.5 |
| Polymer | 4.36 | 4.36 |
| Preservative | 0.8 | 0.8 |
| Silicon | 0.3 | 0.3 |
| Solvents | 8.09 | 8.09 |
| Surfactant | 2 | 2 |
| Hydrogenated starch hydrolysate | — | 1.43 |
| Disodium cocoamphodiacetate | — | 1.59 |

A half head study was conducted on mannequin heads having curly hair to assess the curl definition effect of compositions including a sugar and chelating agent according to the disclosure, compared to comparative compositions not including a sugar and chelating agent.

For each mannequin head, the hair of the mannequin head was first cleansed with a commercially available shampoo. While the hair was still wet or damp, a sufficient amount of composition 1 was applied to one half-head of each mannequin and distributed evenly onto the hair with the fingers. Approximately the same amount of composition 2 was then applied to the other half of the head, and similarly distributed evenly. The hair on both sides of the mannequin head was then styled and allowed to air dry. After the hair was completely dry, the mannequin was put into a humidity chamber at 80% relative humidity (RH) at 25° C. and monitored after 1 hour.

The hair treated with test composition 2 had better curl definition, frizz control, and the hair had a more natural and less coated feel than the hair treated with composition 1. Additionally, test composition 2 showed better curl pick-up and the curls started closer to the root.

Example 6. pH Dependence

In order to demonstrate the effect of pH according to the disclosure, the following compositions of varying pH values were prepared as shown in Table 10.

TABLE 10

| Formulations | | | | | |
|---|---|---|---|---|---|
| Sample | pH | pH Adjustor | Chelating Agent at 0.5% | Hydrogenated starch hydrolysate | Water |
| AC | 3.8 | Citric acid | Disodium Cocoamphodiacetate | 1% | 98.5% |
| AD | 5.3 | Citric acid | Disodium Cocoamphodiacetate | 1% | 98.5% |
| AE | 8.6 | None | Disodium Cocoamphodiacetate | 1% | 98.5% |
| AF | 11.6 | Sodium hydroxide | Disodium Cocoamphodiacetate | 1% | 98.5% |
| M | 11 | — | Trisodium HEDTA | 1% | 98.5% |

Each composition in Table 10 was tested on natural, curly hair swatches. Each hair swatch was first washed with a commercially available shampoo and detangled. The swatches were then air dried, and sprayed with water five times per swatch. While the swatches were still damp, equal amounts of a testing composition was applied to each hair swatch and then styled. After the swatches air dried, they were put into a humidity chamber at 80% relative humidity at 25° C. for one hour.

After one hour in the humidity chamber, the treated swatches were qualitatively assessed for curl definition, frizz control, and sensory profile. A rating of 1-5 was provided for frizz control and curl definition, where 1 represented the least amount of frizz control/definition and 5 represented the most. The sensory profile was determined by manually palpating each swatch. A description of coated was given when the hair had a coated feel which was a neutral description.

The following Table 11 shows the results of assessment and scores of the visual properties of the hair swatches treated with the testing compositions.

TABLE 11

| Assessment after humidity chamber | | | | | |
|---|---|---|---|---|---|
| | AC | AD | AE | AF | M |
| Curl Definition* | 4 | 4 | 3 | 1 | 1 |
| Frizz Control* | 3 | 4 | 3 | 1 | 2 |
| Sensory Profile | Smooth, buttery coated feel | Smooth, buttery coated feel | Smooth, buttery coated feel | Smooth, buttery coated feel | Some slip, not buttery |

*Scale from 1 to 5, where 1 = least amount of curl definition/frizz control and 5 = most amount of curl definition/frizz control As shown in Table 11, swatches AC-AE with the lower pH showed better frizz control and curl definition than samples AF and M that had a pH of 11 and above. Sample AF and M were puffier and had a loss of curl definition. The sensory profile of all samples was similar. Sample AD had the best frizz control and curl definition with a pH of 5.3.

The invention claimed is:
1. A hair styling composition, comprising:
(a) from 0.2% to 5% by weight based on the total weight of the composition of at least one chelating agent,
(b) from 0.5% to 2% by weight based on the total weight of the composition of at least one sugar, and

(c) at least one cosmetically acceptable solvent,
wherein the pH of the composition is between 3 and 9.

2. The composition of claim 1, wherein the pH ranges from 4 to 6.

3. The composition of claim 1, wherein the at least one chelating agent is chosen from trisodium ethylene diamine, trisodium HEDTA, disodium cocoamphodiacetate, tetrasodium glutamate diacetate, or a mixture thereof.

4. The composition of claim 1, wherein the at least one chelating agent is present in an amount ranging from 0.2% to 0.5% by weight based on the total weight of the composition.

5. The composition of claim 1, wherein the at least one sugar is chosen from glucose, erythritol, glucosamine HCl, and hydrogenated starch hydrolysate.

6. The composition of claim 1, wherein the at least one sugar is present in an amount ranging from 0.5% to 1% by weight based on the total weight of the composition.

7. The composition of claim 1, further comprising at least one polymer chosen from VP/dimethylaminoethyl methacrylate copolymer, polyquaternium-37, or a mixture thereof.

8. The composition of claim 1, further comprising at least one surfactant chosen from glyceryl stearate, PEG-100 stearate, or a mixture thereof.

9. The composition of claim 1, further comprising at least one fatty compound chosen from isopropyl myristate, *Ricinus communis* seed oil, cetearyl alcohol, cetyl esters or the mixtures thereof.

10. The composition of claim 1, wherein the composition is a leave-in composition.

11. The composition of claim 1, wherein the composition improves curl definition.

12. The composition of claim 1, wherein the composition improves frizz control.

13. A method for styling and or caring for hair comprising applying to the hair a composition comprising:

(a) from 0.2% to 5% by weight based on the total weight of the composition of at least one chelating agent,
(b) from 0.5% to 2% by weight based on the total weight of the composition of at least one sugar, and
(c) at least one cosmetically acceptable solvent,
wherein the pH of the composition is between 3 and 9.

14. The method of claim 13, wherein the composition is applied to damp hair.

15. The method of claim 13, wherein the hair was dried by towel.

16. A hair styling composition, comprising:
(a) at least one chelating agent;
(b) from 0.5% to 2% by weight based on the total weight of the composition of at least one sugar, and
(c) at least one cosmetically acceptable solvent
wherein the amount of the chelating agent is 0.2% to 5% by weight of the total composition.

17. The composition of claim 1, wherein the at least one chelating agent is present in an amount ranging from 0.2% to 0.5% by weight based on the total weight of the composition and wherein the at least one sugar is present in an amount ranging from 0.5% to 1% by weight based on the total weight of the composition.

18. A hair styling composition, comprising:
(a) from 0.2% to 0.5% by weight based on the total weight of the composition of at least one chelating agent chosen from trisodium ethylene diamine, trisodium HEDTA, disodium cocoamphodiacetate, tetrasodium glutamate diacetate, or a mixture thereof;
(b) from 0.1% 0.5% to 1% by weight based on the total weight of the composition of at least one sugar chosen from glucose, erythritol, glucosamine HCl, and hydrogenated starch hydrolysate; and
(c) at least one cosmetically acceptable solvent;
wherein the pH of the composition is between 3 and 9.

* * * * *